(12) United States Patent
Hu et al.

(10) Patent No.: US 10,822,300 B2
(45) Date of Patent: Nov. 3, 2020

(54) PROCESS FOR PRODUCING LONG CHAIN AMINO ACIDS AND DIBASIC ACIDS

(71) Applicant: Vitaworks IP, LLC, North Brusnwick, NJ (US)

(72) Inventors: Songzhou Hu, Princeton, NJ (US); Zhen Song, Shanghai (CN)

(73) Assignee: VITAWORKS IP, LLC, North Brunswick, NJ (US)

( * ) Notice: Subject to any disclaimer, the term of this patent is extended or adjusted under 35 U.S.C. 154(b) by 0 days.

(21) Appl. No.: 16/436,470

(22) Filed: Jun. 10, 2019

(65) Prior Publication Data

US 2019/0292134 A1 Sep. 26, 2019

Related U.S. Application Data

(63) Continuation-in-part of application No. 15/880,293, filed on Jan. 25, 2018, now Pat. No. 10,343,978, which is a continuation-in-part of application No. 15/644,708, filed on Jul. 7, 2017, now Pat. No. 10,065,921.

(51) Int. Cl.
*C07C 229/08* (2006.01)
*C07C 209/50* (2006.01)
*C07C 51/06* (2006.01)

(52) U.S. Cl.
CPC ............ *C07C 229/08* (2013.01); *C07C 51/06* (2013.01); *C07C 209/50* (2013.01)

(58) Field of Classification Search
CPC ...... C07C 51/06; C07C 209/50; C07C 229/08
USPC ....................................................... 554/114
See application file for complete search history.

(56) References Cited

U.S. PATENT DOCUMENTS

| 2,462,855 | A | 3/1949 | Genas |
| 4,496,736 | A | 1/1985 | Bonse et al. |
| 5,498,733 | A | 3/1996 | Ayorinde |
| 6,218,574 | B1 | 4/2001 | Liu et al. |
| 6,777,213 | B2 | 8/2004 | Staley |

(Continued)

FOREIGN PATENT DOCUMENTS

| CN | 102089272 A | 6/2011 |
| CN | 102329224 A | 1/2012 |

(Continued)

OTHER PUBLICATIONS

Piazza George J. et al. A Novel Technique for the Preparation of Secondary Fatty Amides II: The Preparation of Ricinoleamide from Castor Oil. JAOCS. Jul. 1993.*

(Continued)

*Primary Examiner* — Deborah D Carr
(74) *Attorney, Agent, or Firm* — Lerner, David, Littenberg, Krumholz & Mentlik

(57) ABSTRACT

There is disclosed a process for the production of dodecanedioic acid and 11-aminoundecanoic acid, comprising: (1) reacting castor oil with a primary or secondary amine to form a amide; (2) isomerizing the amide in the presence of a catalyst to form ketoamide; (3) reacting the ketoamide with hydroxylamine to form the oximeamide; (4) subjecting the oximeamide to Beckmann rearrangement to yield a mixture of two diamides; and (5) hydrolyzing the mixed diamides to produce dodecanedioic acid, 11-aminoundecanoic acid, hexylamine and heptanoic acid.

10 Claims, 5 Drawing Sheets

(56) References Cited

U.S. PATENT DOCUMENTS

| | | |
|---|---|---|
| 8,431,728 B2 | 4/2013 | Pees |
| 8,729,298 B2 | 5/2014 | Zang et al. |
| 9,969,676 B1 | 5/2018 | Hu |
| 9,969,678 B2 | 5/2018 | Kanaya |
| 10,053,416 B1 | 8/2018 | Hu |
| 10,065,921 B1 * | 9/2018 | Hu .................. C07C 231/10 |
| 2004/0082042 A1 | 4/2004 | Staley |
| 2011/0105774 A1 | 5/2011 | Dubois |
| 2011/0251414 A1 | 10/2011 | Pees |
| 2019/0016668 A1 | 1/2019 | Hu |

FOREIGN PATENT DOCUMENTS

| | | |
|---|---|---|
| CN | 102476990 A | 5/2012 |
| CN | 102795989 A | 11/2012 |
| CN | 103497100 A | 1/2014 |
| CN | 103804209 A | 5/2014 |
| CN | 104447274 A | 3/2015 |
| CN | 104447280 A | 3/2015 |
| CN | 104496793 A | 4/2015 |
| CN | 104529741 A | 4/2015 |
| CN | 104529747 A | 4/2015 |
| CN | 104591998 A | 8/2016 |
| WO | 2017088218 A1 | 6/2017 |

OTHER PUBLICATIONS

Yu Xiuzhu et al. Simple Synthesis Hydrogenated Castor Oil Fatty Amide Wax and Its Coating Characterization. J Oleo Sci. Jul. 1, 2017; 66(7): 659-665.*

Bil YK Alexander et al. A Novel Technique for the Preparation of Secondary Fatty Amides. JAOCS. May 1992. 69(5): 488-491.*

Besson Michele et al. Conversion of Biomass into Chemical over Metal Catalysts. Chem. Rev. Feb. 12, 2014; 114(3): 1827-70.*

A. Chauvel & G. Lefebvre, Petrochemical Processes 2: Major Oxygenated, Chlorinated and Nitrated Derivatives, pp. 274-286, Institut Francais de Petrole Publications; Editions Technip; 1989.

W. L. Kohlhase, E.H. Pryde, & J.C. Cowan, J. Am. Oil Chemists Soc., 1970, vol. 47, pp. 183-188.

Perkins, R.B., Roden, J.J. & Pryde, E.H.; Nylon-9 from unsaturated fatty derivatives: Preparation and characterization; J Am Oil Chem Soc (1975) vol. 52: No. 11, pp. 473-477. doi:10.1007/BF02637493.

International search report and written opinion issued for corresponding International Patent Application No. PCT/US2018/038997, dated Oct. 25, 2018.

Besson, et al., Conversion of Biomass into Chemical over Metal Catalysts, Chemical Reviews, Feb. 2014, pp. 1827-1870, 114(3).

Bilyk et al., A Novel Technique for the Preparation of Secondary Fatty Amides, JAOCS, May 1992, pp. 488-491, 59(5).

International Search Report including Written Opinion for Application No. PCT/US2019/057461, dated Feb. 20, 2020, pp. 1-9.

Piazza, et al., A Novel Technique for the Preparation of Secondary Fatty Amides II: The Preparation of Ricinoleamide from Castor Oil, JAOCS, Jul. 1993, pp. 727-729, 70(7).

Yu, et al., Simple Synthesis Hydrogenated Castor Oil Fatty Amide Wax and Its Coating Characterization, Journal of Oleo Science, 2017, pp. 659-665, 66(7).

* cited by examiner

PROCESS FOR PRODUCING LONG CHAIN AMINO ACIDS AND DIBASIC ACIDS

CROSS REFERENCE TO RELATED APPLICATIONS

This application is a continuation-in-part of the application Ser. No. 15/880,293, filed on Jan. 25, 2018, which is a continuation-in-part of the application Ser. No. 15/644,708, filed on Jul. 7, 2017, now U.S. Pat. No. 10,065,921, all of which are incorporated herein by reference.

TECHNICAL FIELD

The present invention relates to a method for the production of monomers for long chain nylons, more specifically, it relates to a process for the production of long chain amino acids and dibasic acids.

BACKGROUNDS OF THE INVENTION

Long chain saturated aliphatic amino acids, lactams, and dibasic acids are important monomers for long chain nylons and engineering plastics. Nylons are a class of polymers that contain amide bond on their backbone of chains. Nylons are one of the most widely used, most numerous in types, and most consumed class of engineering plastics.

Because of their unusual molecular structure, long chain nylons possess extraordinary physical properties, i.e., higher mechanical strength than metal, low hygroscopicity, excellent resistance to oil, low temperature, abrasion, and chemical corrosion, and most importantly, easy to fabricate. Long chain nylons are made into many kinds of plastics products, spun to fibers, and stretched to thin films. Long chain nylons are also used in paints and hot melt adhesives. Hence, long chain nylons find wide applications in automobile, electrical, electronic, telecommunications, petrochemical, and aerospace industries.

Long chain amino acids and lactams are used industrially as monomers to produce nylon-9, nylon-11, and nylon-12.

Long chain dibasic acids are condensed with diamines industrially as starting materials to produce nylon-610, nylon-612, nylon-510, nylon-512, nylon-1010, and nylon-1212.

Among the current production technologies, the nylon-9 monomer, 9-aminononanoic acid is produced from oleic acid or oleonitrile by a series of chemical reactions (details are described in J. Am. Oil Chemist's Soc., 1975, Vol. 52, No. 11, pp 473-477).

For the nylon-11 monomer, 11-aminoundecanoic acid, is produced from castor oil through ester exchange with methanol, pyrolysis at high-temperature, free radical addition of anhydrous hydrogen bromide, and finally ammonolysis (detailed process is described by A. Chauvel & G. Lefebvfre, Petrochemical Processes 2: Major Oxygenated, Chlorinated and Nitrated Fatty acids, pp 274-278). The overall yield is not more than 55%.

The monomer of nylon-12, laurolactam, is produced from 1,3-butadiene through a series of reactions, i.e., trimerization to cyclododecatriene, hydrogenation to cyclododecane, oxidation to cyclododecanol or cyclododecanone, oximation, and Beckmann rearrangement (detailed process is described by A. Chauvel & G. Lefebvfre, Petrochemical Processes 2: Major Oxygenated, Chlorinated and Nitrated Fatty acids, pp 279-286).

In the industrial production of long chain dibasic acids, azelaic acid is produced from oleic acid by oxidation, while sebacic acid is produced by alkaline scission of castor oil or fatty acids at high temperature (200° C. to 250° C.), followed by purification and refining.

For the important dodecanedioic acid, there are two industrial processes of quite different nature. One is the chemical synthesis from 1,3-butadiene through catalyzed trimerization to cyclododecatriene, hydrogenation to cyclododecane, oxidation to cyclododecanol or cyclododecanone, and finally, oxidation by nitric acid. The other process is more preferable, i.e., biochemical oxidation of terminal methyl groups of high purity dodecane or lauric acid by fermentation.

In the production of these monomers by chemical synthesis, there exist problems for the current industrial processes, e.g., low overall yield (35% for 9-aminononanoic acid, 55% for 11-aminoundecanoic acid, 80% for sebacic acid), reaction conditions that are inherently dangerous and difficult to control. For example, the production of 9-aminononanoic acid requires the use of ozone, and the production of 11-aminoundecanoic acid requires a pyrolysis reaction at high temperature. Moreover, the production of laurolactam and dodecanedioic acid makes use of trimerization of 1,3-butadiene under inert reaction conditions with a flammable catalyst, while the production of sebacic acid requires a very corrosive alkaline scission of castor oil.

Although the reaction conditions are mild, fermentative oxidation of long chain alkanes or lauric acid via fermentation to produce dodecanedioic acid or other long chain dibasic acids, yields a crude product that contains a large amount of biomaterials and degraded short chain dibasic acids. To obtain a product suitable for the production of nylons, crude product must be subjected to complicated purification and refinement. Many methods to refine and purify the crude products are described in the literature. Detailed processes are disclosed in U.S. Pat. Nos. 6,218,574; 8,729,298; CN 104591998A; CN 102476990A; CN 102329224A; CN 103497100A; CN 102795989A; CN 104447274A; CN 104447280A; CN 104496793A; CN 104529741A; and CN 104529747A.

WO 2017088218 by the present inventor discloses a novel process for the co-production of long chain amino acid and dibasic acid. According to the disclosed process, keto fatty acid ester or amide is reacted with hydroxylamine to form an oxime fatty acid derivative, which is subjected to the Beckmann rearrangement to form a mixture of two amide fatty acid derivatives. When the mixed amide derivatives are hydrolyzed, a mixture of long chain amino acid and dibasic acid is obtained and separated in high dilution.

The process according to WO 2017088218 starts from an inconvenient starting material, i.e., keto fatty acid ester or amide, which is not commercially available. Moreover, during the preparation of oxime, the ester is not stable and is hydrolyzed to produce a significant amount of an alkali salt of oxime fatty acid, which is soapy and renders processing difficult. Furthermore, this impurity interferes with the Beckman rearrangement by inactivating the catalyst.

It is an object of the present invention to overcome the disadvantages by disclosing a process for producing long chain amino acid and dibasic acid from hydroxy fatty acid, in particular, 12-hydroxystearic acid, which is a commercially available, stable starting material.

It is another object of the present invention to disclose a process for producing 11-aminoundecanoic acid and dodecanedioic acid from castor oil, which is bio-renewable, commercially and economically available in large scale.

DESCRIPTION OF THE INVENTION

It is an object of the present invention to overcome the disadvantages of current industrial processes and to disclose a process for the coproduction of long chain amino acids and dibasic acids. In comparison to current industrial processes, the process disclosed in the present invention utilizes mild reaction conditions, provides a high overall yield, and is particularly suitable for industrial production.

Figure 1:
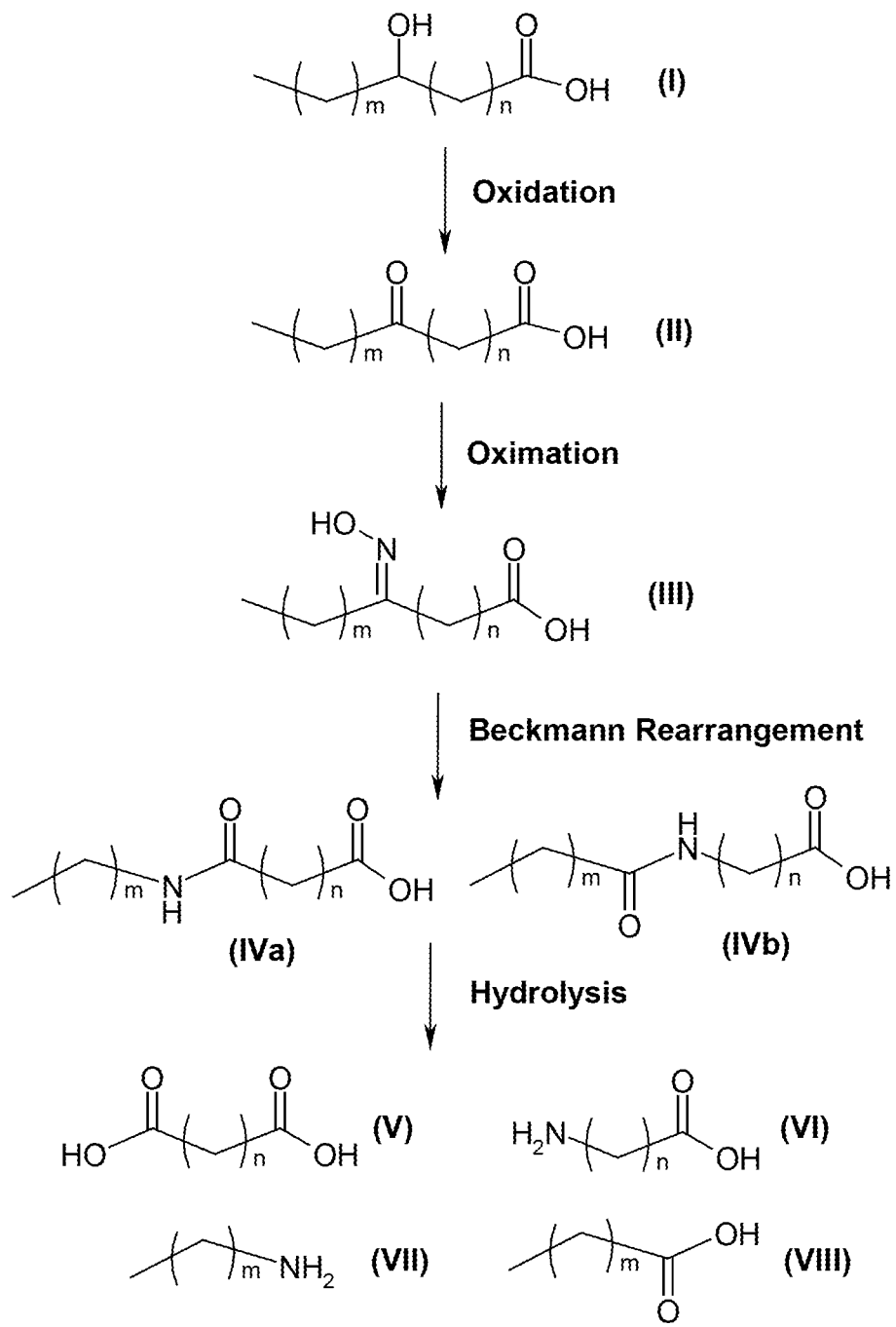
FIG. 1. Reaction scheme for producing long chain amino acid and dibasic acid from hydroxy fatty acid.
Figure 2:
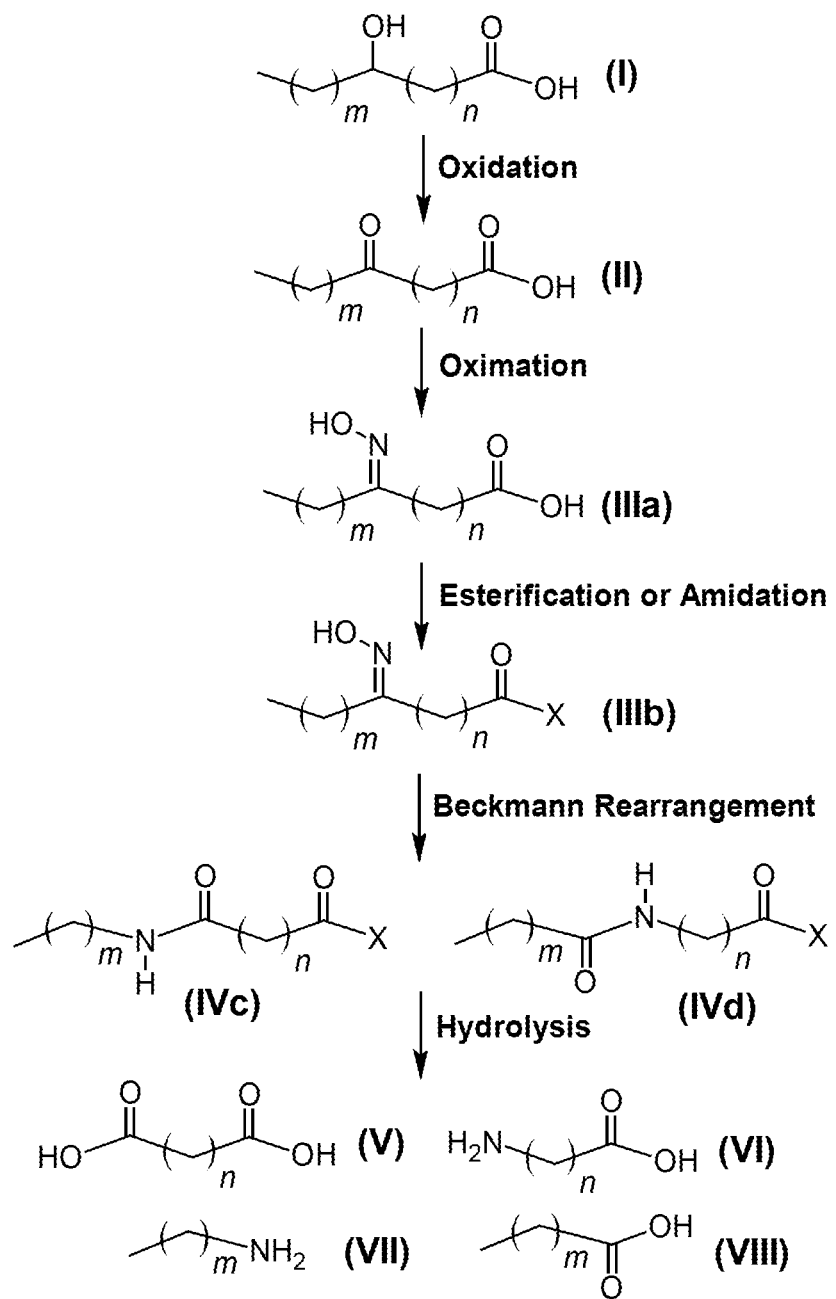
FIG. 2. Reaction scheme for producing long chain amino acid and dibasic acid from hydroxy fatty acid via an intermediate ester or amide.

The present invention employs commercially available hydroxy fatty acid (I) as starting material to produce long chain dibasic acids (V) and amino acids (VI), according to the reaction scheme schematically illustrated in the FIG. 2, wherein m is an integral of 0 to 10; n is an integral of 6 to 20. The process according to the present invention proceeds according to the following steps:

(1) oxidizing the starting material, hydroxy fatty acid (I), to keto fatty acid (II);
(2) reacting a keto fatty acid (II) with a solution of hydroxylamine to form an oxime fatty acid (IIIa) or subjecting a keto fatty acid to an ammoximation reaction to form an oxime fatty acid (IIIa) in the presence of an organic solvent;
(3) reacting the oxime fatty acid with an alcohol or a primary amine or secondary amine to yield an oxime fatty acid ester or an oxime fatty acid amide (IIIb).
(4) subjecting the oxime fatty acid ester or amide (IIIb) to the Beckmann rearrangement to form a mixture of amide fatty acid ester or amide of the structure (IVc) and (IVd) in the presence of one or more catalysts;
(5) hydrolyzing the mixed amide fatty acid ester or amide of the structure (IVc) and (IVd) to yield long chain dibasic acid (V), long chain amino acid (VI), short chain primary alkylamine (VII), and short chain alkanoic acid (VIII); and
(6) separating long chain dibasic acid (V), long chain amino acid (VI), and alkanoic acid (VIII) from their respective alkali salt.

It is noted that the starting material is 12-hydroxystearic acid, when m=5, n=10. According to the process disclosed in the present invention, the monomer of nylon-11, 11-aminoundecanoic acid is coproduced along with dodecanedioic acid, an important monomer for the production of nylon 612 and nylon 1212.

When m=7, n=8, the starting material is 10-hydroxystearic acid. According to the process disclosed in the present invention, 9-aminononanoic acid, the monomer for nylon-9 is coproduced along with sebacic acid, which is used in the production of nylon 610 and nylon 1010.

When m=5, n=12, the starting material is 14-hydroxyarachidic acid. According to the process disclosed in the present invention, 13-aminotridecanoic acid, the monomer for nylon-13, is coproduced along with tetradecanedioic acid (i.e., brassylic acid).

Oxidation of hydroxy fatty acid (I) to keto fatty acid (II) can be performed with sodium hypochlorite or calcium hypochlorite in an aqueous acetic acid at a temperature from 0° C. to 40° C., preferably, from 0° C. to 20° C. After the oxidation reaction is completed, acetic acid is removed by distillation, and the residual is suspended with water to dissolve sodium chloride or calcium chloride. The keto fatty acid (III) is recovered by means of solid-liquid separation.

Oxidation of hydroxy fatty acid (I) to keto fatty acid (II) can also be carried out with hydrogen peroxide with a tungsten or a molybdenum compound as catalyst in the presence of a phase transfer catalyst. The oxidation of hydroxy fatty acid with hydrogen peroxide can be carried out in the presence of an organic solvent, more preferably, in the absence of an organic solvent. After the oxidation is completed, molten keto fatty acid is separated from aqueous solution by a phase separation at a temperature from 50° C. to 90° C.

In order to obtain the oxime fatty acid (IIIa), a keto fatty acid (II), is dissolved in an organic solvent and reacted with an aqueous solution of hydroxylamine salt with a basic agent to adjust the pH of the reaction mixture.

The organic solvent for the oximation reaction can be either water soluble or water insoluble. The requirement for a selected solvent is that the solvent can dissolve both the keto fatty acid (II) and oxime fatty acid (IIIa), and does not react with starting material, product, and hydroxylamine. For example, aldehydes and ketones as solvents are not suitable for preparing oxime, because the solvents will react with hydroxylamine. Nitriles are also not suitable as the nitrile group can react with hydroxylamine. Amines will react with ketone to form Schiff base and are therefore not suitable solvents.

Suitable solvents belong to the classes of alcohols, esters, aliphatics, aromatics, ethers, and amides. Preferable solvents are, but not limited to, methanol, ethanol, propanol, isopropanol, n-butanol, isobutanol, sec-butanol, tert-butanol, amyl alcohols, hexanols, cyclohexanol, ethyl acetate, butyl acetate, isobutyl acetate, propyl acetate, isopropyl acetate, ethyl propionate, propyl propionate, isopropyl propionate, propyl formate, butyl formate, isobutyl formate, benzene, toluene, xylenes, cumene, trifluoromethylbenzene, diethyl ether, dipropyl ether, dibutyl ether, diisopropylether, tetrahydrofuran, methyltetrahydrofuran, dioxane, dimethyl formamide, dimethyl acetamide, N-methyl pyrrolidone, tetramethylurea, dichloromethane, di chloroethane, chloroform, and a mixture of two or more thereof.

The most preferable solvent is toluene.

It is found that the oximation reaction can be performed in the absence of organic solvent. An oil phase of molten keto fatty acid (II) is reacted with an aqueous solution of hydroxylamine salt with a basic agent to adjust the pH of aqueous reaction solution. After the reaction, the product (IIIa) is simply separated by a phase separation from aqueous phase and dehydrated for the next stage of the process.

A hydroxylamine salt is selected from the group consisting of hydroxylamine hydrochloride, hydroxylamine sulfate, and hydroxylamine acetate. An aqueous solution of hydroxylamine can also be used.

A basic agent, used to maintain pH of the oximation reaction, is selected from the group consisting of alkali and ammonium salts of hydroxide, bicarbonate, carbonate, sulfite, bisulfite, phosphate, and carboxylate. The alkali metals are lithium, sodium, potassium, or cesium.

Suitable basic agents are, but not limited to, sodium hydroxide, potassium hydroxide, sodium bicarbonate, sodium carbonate, potassium bicarbonate, potassium carbonate, ammonium hydroxide, ammonia, ammonium carbonate, ammonium bicarbonate, sodium formate, sodium acetate, potassium formate, potassium acetate, ammonium phosphate, sodium phosphate, and a mixture of two or more thereof.

The most preferable agent is ammonium hydroxide.

It is necessary to maintain a proper pH in order for the oximation to proceed to completion. Although oximation reaction can proceed at a pH in the range from 2 to 10, it is found that the reaction solution becomes soapy at a pH of 6 and above, so higher pH cannot be used. At a pH lower than 3, oximation reaction proceeds at a very low rate. Thus, it is preferable to maintain the pH in a range from 3 to 6, most preferably in a range of 3.5 to 5.5.

Oximation of a keto fatty acid (II) can also be performed by an ammoximation reaction, i.e., the oxidation of ammonia by hydrogen peroxide in the presence of Ti-catalyst. Keto fatty acid is dissolved in an organic solvent, most preferably, toluene. Ammonia and hydrogen peroxide can be added concomitantly, sequentially, continuously, semi-continuously, or batch wise.

The oximation reaction is carried out at a temperature from 0° C. to 100° C., but can also be carried out at higher temperature under pressure. This reaction is preferably carried out at a temperature from 40° C. to 100° C. under atmospheric pressure. If the temperature is low, the reaction rate is slow, and reaction time is unnecessarily prolonged. Preferably, the reaction temperature is selected to be 60° C. to 80° C.

The oximation reaction is carried out in the air, but can also be carried out under the protection of inert atmosphere, i.e., nitrogen, argon, or helium.

Time for the completion of oximation is related to the reaction temperature, usually in about 0.5 to 24 hours. Preferably, the reaction time is maintained for 1 to 6 hours, and the reaction temperature is controlled at 0° C. to 100° C. If the reaction time is too short, the residual content of keto fatty acid is too high, the yield will be reduced. Although the residual keto fatty acid can be recovered in the post treatment, additional equipment for recovery will be needed. Prolonged reaction can reduce the residual amount of keto fatty acid, but the volume of reactors becomes unnecessarily large.

Reactor for the oximation reaction can be any reactor conventionally used in the chemical processing, for example, batch stirred reactor, semi-continuous reactor, tubular reactor, or flow reactor. Preferable reactor is continuous stirred tank reactor (CSTR). If CSTR is adopted, an aqueous solution of hydroxylamine and a solution of a keto fatty acid in an organic solvent are simultaneously added in one reactor and then the reaction is completed in a cascade of reactors. On the other hand, the two solutions can be added to a stirred batch reactor concomitantly, sequentially, continuously, semi-continuously, or batch wise.

The molar ratio of hydroxylamine to a keto fatty acid (II) can be from 0.1 to 10.0, preferably 1.0 to 2.0, most preferably 1.05 to 1.1 to ensure that the keto fatty acid is completely converted to the oxime fatty acid (IIIa).

After completion of the oximation reaction, the oxime fatty acid (IIIa) remains dissolved in organic phase, and aqueous phase is separated. Although the solubility of water in organic phase is small, but the remaining trace amount of water will lower the yield of esterification or amidation of the next stage. In order to remove trace amount of water from organic phase, a drying agent may be used. Preferably, the remaining water is removed by distilling part of the solvent. The distilled solvent can be used directly in the step of oximation without being dried. After distillation, the residual anhydrous solution of oxime fatty acid (IIIa) can be directly used for the esterification or amidation reaction.

To prepare an ester of an oxime fatty acid, an alcohol of $C_1$-$C_{12}$ carbons can be used. Aliphatic alcohols or aromatic alcohols can be used. Such alcohols are, but not limited to, methanol, ethanol, propanol, isopropanol, butanol, isobutanol, secondary butanol, pentaol, isopentanol, hexanol, cyclohexanol, octanol, 2-ethylhexanol, and benzyl alcohol. Preferably, the alcohol is methanol or ethanol. Most preferably, the alcohol is methanol.

One or more catalysts can be used to affect the esterification. Preferably, a catalyst or catalysts used to affect the esterification does not hydrolyze the oxime or affect the Beckmann rearrangement for the next step. Suitable catalysts are found among anhydrous acids, such as sulfuric acid, hydrogen halides in an alcohol, aliphatic sulfonic acids, aromatic sulfonic acids, and solid acids. Titanium tetraalkoxides are effective catalysts in forming the ester. Solid acids, such as acidic ion exchanger, are also effective for the formation of esters.

After the esterification is complete, active catalyst is neutralized with a base and excess alcohol is recovered and dehydrated for recycling. In the case of a solid acid as a catalyst, the catalyst is separated by filtration. The product is preferably dissolved in an organic solvent, washed with water, and thoroughly dried for the Beckmann rearrangement.

To prepare an amide, the oxime fatty acid (IIIa) is condensed with a primary or a secondary amine of the structure of $HNR_1R_2$, wherein $R_1$ and $R_2$ are each independently hydrogen or $C_1$-$C_{12}$ aliphatic or aromatic groups. Suitable amines are, but not limited to, methylamine, ethylamine, propylamine, isopropylamine, butylamine, isobutylamine, secondary butylamine, pentylamine, isopentylamine, hexylamine, cyclohexylamine, heptylamine, octylamine, isooctylamine, dimethylamine, diethylamine, dibutylamine, and benzylamine. Preferably, the amines are short chain primary aliphatic amines of $C_1$-$C_6$. Most preferably, the amine is hexylamine, which is a product in the process for the production of 11-aminoundecanoic acid and dodecanedioic acid.

After completion of the esterification or amidation reaction, the oxime fatty acid ester or amide (IIIb) is dissolved in an organic solvent and dried thoroughly before Beckmann rearrangement. In order to remove trace amount of water from organic phase, a drying agent may be used. Preferably, the remaining water is removed by distilling part of the solvent. After distillation, the residual anhydrous solution of oxime fatty acid ester or amide (IIIb) can be directly used for the Beckmann rearrangement.

For the Beckmann rearrangement, the required solvents have to show good solubility towards both an oxime fatty acid ester or amide (IIIb) and mixed amide fatty acids ester, (IVc) and (IVd), and can dissolve catalyst for the Beckmann rearrangement and will not react with the catalyst.

A solvent for Beckmann rearrangement must be stable and amenable to recover. Different solvents can be used for the oximation reaction and the Beckmann rearrangement to satisfy the requirement of each reaction. Preferably, a single solvent is used to satisfy the requirement of both reactions in order to reduce the use and recycling of solvent. More preferably, the selected solvent is not water-soluble so that it can be easily separated after the oximation reaction and the Beckmann rearrangement. The amount of solvent used in both reactions is not particularly limited as the solvent only functions to dissolve the reactants and products.

Solvents that show the required properties for the Beckmann rearrangement belong to the classes of ester, aliphatics, aromatics, and ethers. Preferable solvents are, but not limited to, butyl acetate, ethyl acetate, benzene, toluene, xylene, cumene, anisole, diethyl ether, diisopropyl ether, dibutyl ether, methyl tert-butyl ether, ethyl tert-butyl ether, methyl tetrahydrofuran, petroleum ether, cyclohexane, dichloroethane, methylene chloride, chloroform, carbon tetrachloride, and trifluoromethylbenzene, acetonitrile, propionitrile, butyronitrile, benzonitrile, and a mixture of two or more thereof.

The most preferable solvent is toluene.

After thorough drying, the oxime fatty acid ester or amide (IIIb) is subjected to the Beckmann rearrangement to a mixture of two amide fatty acids derivatives (IVc) and (IVd) in the presence of one or more catalysts.

Suitable catalysts are, but not limited to, activated chlorine compounds, sulfuric acid, alkylsulfonic acid, arylsulfonic acid, perfluorocarboxylic acids, trifluoroacetic acid, and Lewis acids.

Acetic acid containing hydrogen chloride, hydrogen bromide, or anhydride is also a suitable catalyst.

Suitable activated chlorine compounds are, but not limited to, thionyl chloride, sulfuryl chloride, chlorosulfonic acid, various sulfonyl chlorides: i.e., methanesulfonyl chloride, toluenesulfonyl chloride, various carbonyl chlorides: i.e., formyl chloride, acetyl chloride, benzoyl chloride, oxalyl chloride, phosgene, diphosgene, triphosgene, boron trichloride, chlorine-containing phosphorus compounds: i.e., phosphorus trichloride, phosphorus pentachloride, oxyphosphoryl chloride, and chlorine-containing heterocycles: i.e., cyanuric chloride, phosphorazine. One or a combination of two or more compounds can be used as catalyst.

Suitable Lewis acids are metal halides, i.e., zinc chloride, ferric chloride, cobalt chloride, stannous chloride, aluminum chloride, titanium chloride, boron trichloride, and a mixture of two or more thereof.

In the Beckmann rearrangement as described above, activated chlorine-containing compound is used in catalytic amount, i.e., less than 10% of the molar amount of the oxime derivative, preferably in an amount of 0.1 to 5%. As with activated chlorine-containing compound, Lewis acid is also used in catalytic amount, i.e., less than 10% of the molar amount of the oxime derivative, preferably in an amount of 0.1 to 5%.

When sulfuric acid is used in the Beckmann rearrangement, the amount can be determined according to methods known in prior art for the Beckmann rearrangement.

The molar ratio of Lewis acid and activated chlorine-containing compound is 1:0.01 to 1:100, preferably between 1:0.3 to 1:1.5.

The amount of catalyst, reaction temperature, reaction pressure, and reaction time are related. Under certain temperature, reaction time can be shortened by increasing the amount of catalyst.

The temperature for the Beckmann rearrangement of an oxime fatty acid ester or amide (IIIb) is not strictly limited, from room temperature to refluxing temperature. The reaction can also be performed at higher temperature under increased pressure. But if the temperature is too high, the color of rearranged products will darken, rendering post-treatment difficult.

The Beckmann rearrangement can be carried out in atmosphere, but also under inert gases, i.e., nitrogen, argon, or helium as protective atmosphere. This reaction is preferably carried out in dry air. The pressure for carrying out the rearrangement reaction is not limited, from standard normal pressure, to reduced or increased pressure.

The reactor for the Beckmann reaction is not limited. Reactors commonly used in chemical industry, and tubular reactors are suitable. The reaction can be carried out in batch, semi-continuously, or continuously.

After the Beckmann rearrangement, the product of an amide fatty acid derivatives is obtained as a mixture of two amides of the structure (IVc) and (IVd), in an almost equal molar ratio. After recovery of solvent, this mixture can be purified to obtain pure amide fatty acid before proceeding to a hydrolysis step. On the other hand, crude product of the rearrangement reaction can be directly subjected to hydrolysis, and the impurities can be removed after hydrolysis. In fact, if the purity of oxime fatty acid ester or amide (IIIb) is good, the rearrangement product is nearly pure.

The hydrolysis of the mixed amide fatty acid derivatives can be carried out with an acid. Suitable acids are sulfuric acid, hydrochloric acid, hydrobromic acid, hydroiodic acid, or nitric acid. One or a combination of two or more acids in any ratio can be used for the hydrolysis reaction. The amount of acid used in hydrolysis reaction and reaction conditions can be determined by those skilled in art. In order to increase the solubility of mixed amide fatty acid derivatives during the hydrolysis, the reaction system may be added some organic solvents. Suitable solvents are, but not limited to, methanol, ethanol, formic acid, and acetic acid.

After hydrolysis, long chain dibasic acid and short chain alkanoic acid are present in the form of carboxylic acid, while alkylamine and long chain amino acid are present as their acid salts. Preferably, water is introduced to dilute the hydrolysis suspension, and after cooling, long chain dibasic acid is crystallized and alkanoic acid is present in the form of an oil. After filtration and extensive washing first with water, then with a lower alcohol to remove alkanoic acid, long chain dibasic acid is isolated. Short chain alkanoic acid is isolated from the acidic mother liquor by a phase separation, since alkanoic acid, i.e., heptanoic acid, is insoluble in water.

The mother liquor is then neutralized with a basic agent to a pH in the range from 5.0 to 7.0 to precipitate the long chain amino acid. The precipitated long chain amino acid is isolated by means of solid-liquid separation and washed extensively with deionized water. The obtained long chain dibasic acid and amino acid can be purified by recrystallization to yield products of desired quality.

After the separation of long chain amino acid, the mother liquor is neutral and contains a neutral salt of alkylamine. In order to recover alkylamine, a basic agent is added to the mother liquor and alkylamine can be distilled from the strongly alkaline solution.

A basic agent is selected from the group consisting of ammonia, ammonium hydroxide, lithium hydroxide, sodium hydroxide, potassium hydroxide, ammonium bicarbonate, ammonium carbonate, sodium bicarbonate, sodium carbonate, potassium bicarbonate, potassium carbonate, ammonium acetate, sodium acetate, potassium acetate, and a mixture of two or more thereof.

Preferable basic agent is selected from alkali salts of hydroxide. The most preferable basic agent is sodium hydroxide.

The mixed amide fatty acid derivatives of the formula (IVc) and (IVd) can also be hydrolyzed with a basic agent. The amount of base used in the reaction and reaction conditions can be determined by those skilled in art. Suitable base is selected from the group consisting of sodium hydroxide, potassium hydroxide, sodium carbonate, potassium carbonate, barium hydroxide, and a mixture of two or more thereof. The most preferable base is sodium hydroxide.

Solvent for the hydrolysis reaction is water, or an aqueous mixture of organic solvents. Suitable organic solvents are, but not limited to, methanol, ethanol, isopropanol, tetrahydrofuran, dioxane, and a mixture of two or more thereof.

The temperature for the hydrolysis reaction is in the range of 50° C. to 200° C., preferably from 100° C. to 150° C. Pressure during the hydrolysis is from autogenous to increased pressure. The hydrolysis reaction can be carried out in atmosphere, but also under the protection of inert atmosphere.

The time for the hydrolysis reaction is determined by alkali hydroxide concentration, reaction temperature, from 1 to 24 hours. Preferably the reaction time is from 2 to 4 hours. If the reaction is too short, the hydrolysis is not complete. If the reaction time is too long, the volume of reactor becomes large, unnecessarily increasing capital investment.

After the hydrolysis, organic solvent, if present, is removed by distillation. Alkylamine, i.e., hexylamine, is also recovered by distillation. The strongly alkaline solution contains alkali salts of long chain dibasic acid, alkanoic acid, and long chain amino acid. These three products are separated in a step-wise neutralization or acidification with an acid.

The acid is selected from the group consisting of sulfuric acid, hydrochloric acid, hydrobromic acid, nitric acid, phosphoric acid, formic acid, acetic acid, propionic acid, malic acid, glycolic acid, tartaric acid, citric acid, sulfamic acid, benzenesulfonic acid, toluenesulfonic acid, xylenesulfonic acid, methanesulfonic acid, ethanesulfonic acid, and a mixture of two or more thereof. Preferably, an inorganic acid is selected.

Most preferably, the acid is sulfuric acid.

First, the solution is neutralized to a pH in the range of 7-8 to precipitate long chain amino acid, which is isolated by means of solid-liquid separation. The mother liquor is then adjusted to a pH in the range from 4-5 to precipitate long chain dibasic acid, which is isolated by means of solid-liquid separation. Finally, the mother liquor is acidified to a pH in the range of 1-3 to yield alkanoic acid, which is isolated by a phase separation as alkanoic acid is insoluble in water. Optionally, the crude alkanoic acid is distilled to afford a product of desired purity.

Figure 3:
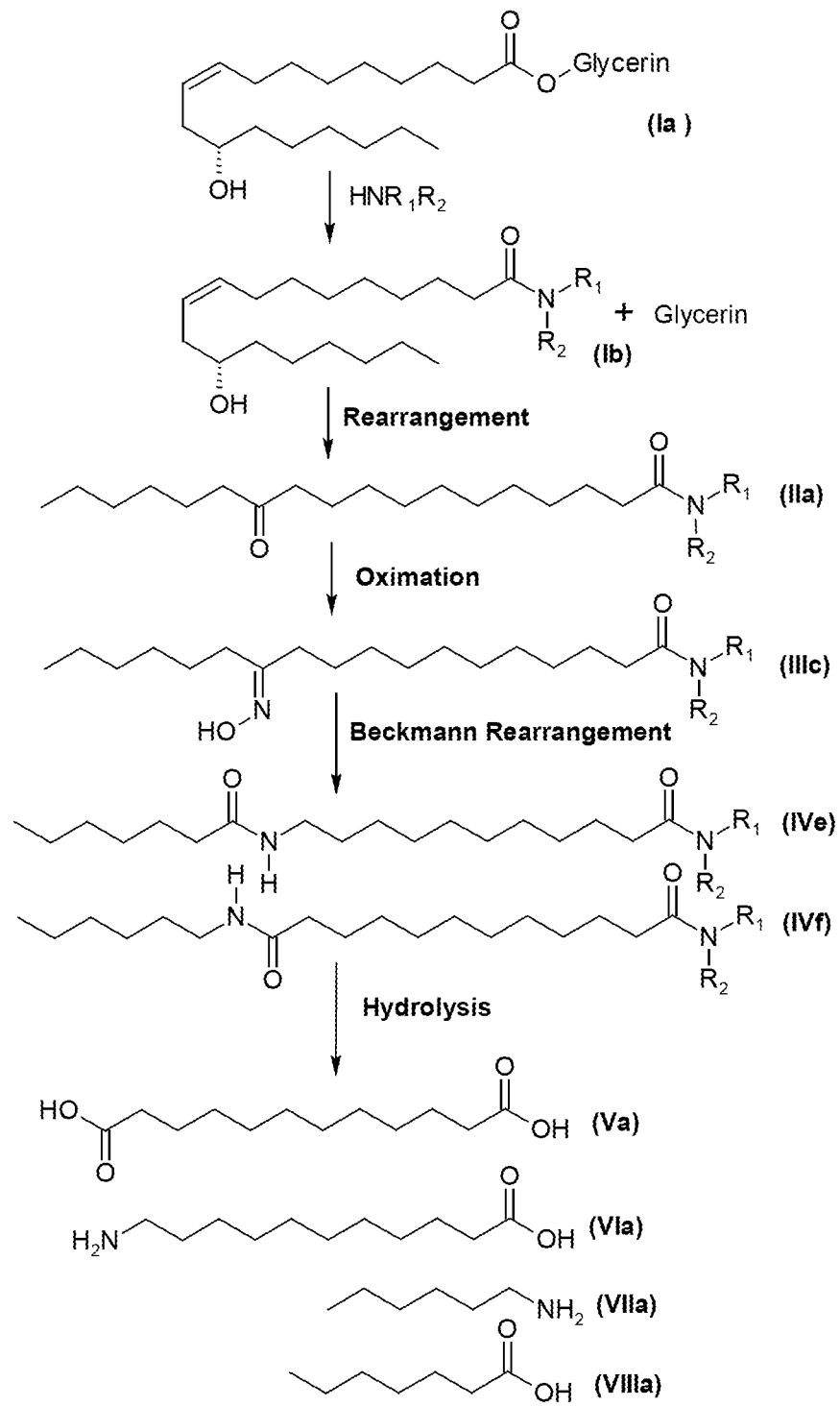
FIG. 3. illustrates one embodiment of a reaction scheme for producing 11-aminoundecanoic acid and dodecanedioic acid from castor oil.

FIG. 3 illustrates one embodiment of a reaction scheme for producing 11-aminoundecanoic acid and dodecanedioic acid from castor oil, which is a widely available industrial oil harvested from castor bean.

The process according to the present invention starts with the production of an amide (Ib) by the reaction of castor oil (Ia) with a primary or a secondary amine of the structure: $HNR_1R_2$, wherein $R_1$ and $R_2$ are each independently hydrogen or $C_1$-$C_{12}$ aliphatic or aromatic groups. Suitable amines are, but not limited to, methylamine, ethylamine, propylamine, isopropylamine, butylamine, isobutylamine, secondary butylamine, pentylamine, isopentylamine, hexylamine, cyclohexylamine, heptylamine, octylamine, isooctylamine, dimethylamine, diethylamine, dibutylamine, and benzylamine. Preferably, the amines are short chain primary aliphatic amines of $C_1$-$C_6$. Most preferably, the amine is hexylamine, which is a product in the process for the production of 11-aminoundecanoic acid and dodecanedioic acid from castor oil.

The reaction of castor oil with the amine $HNR_1R_2$ may be carried out neat or in the presence of a solvent that is inert towards the amine. Preferably, the reaction is carried out neat in the absence of a solvent. The temperature for the formation of amide ranges from room temperature to 250° C., preferably from 60° C. to 210° C., more preferably 90° C. to 180° C., most preferably 120° C. to 160° C. The reaction may be conveniently monitored by disappearance of castor oil from the reaction mixture.

After the amidation reaction is completed, the solution is cooled to below 100° C., but above the melting point of the product. Then warm water is added to the solution to extract glycerol to aqueous phase. After phase separation of the aqueous phase, the oil phase is optionally washed with a dilute acid to remove excess amine. The organic phase is the product amide (Ib), which is obtained in nearly quantitative yield and may be used in the following step without further purification.

The amide (Ib) may be isomerized to a ketoamide (IIa) in the presence of a catalyst. Suitable catalysts are found among pentacarbonyl iron, Raney Nickel, and Pd/C. The isomerization reaction can be carried out in the absence or presence of a solvent. Preferably, the reaction is performed in the absence of any solvent to simplify the process. The temperature for the isomerization reaction to occur may be from 160° C. to 280° C., preferably from 170° C. to 250° C., most preferably from 180° C. to 220° C.

The crude ketoamide (IIa) may be used for the oximation reaction to prepare the oxime amide (IIIc). Preferably, the crude ketoamide (IIa) is recrystallized from a solvent to obtain a purified product. Suitable solvents are lower alcohols and aromatics. Such solvents are methanol, ethanol, propanol, isopropanol, butanol, isobutanol, toluene, and xylenes.

In order to prepare the oxime amide (IIIc), the ketoamide (IIa), dissolved in an organic solvent or in the absence of a solvent, is reacted with aqueous hydroxylamine or is subjected to an ammoximation reaction to form oxime (IIIc). A solvent for the oximation reaction may be either water soluble or water insoluble. The requirement for selecting proper solvent is that the solvent can dissolve both the ketoamide (IIa) and the resulting oximeamide (IIIc), and does not react with starting material, product, and hydroxylamine. For example, aldehydes and ketones as solvents are not suitable for preparing oxime, because the solvents will react with hydroxylamine. Nitriles are also not suitable as the nitrile group can react with hydroxylamine. Amines will react with ketone to form Schiff base and are therefore not suitable solvents.

For Beckmann rearrangement, the required solvents have to show good solubility towards both oxime amide (IIIc) and mixed diamide (IVe and IVf), and can dissolve catalysts for Beckmann rearrangement and will not react with the catalysts.

A solvent for both the oximation and Beckmann rearrangement must be stable and amenable to recover. Different solvents can be used for the oximation reaction or Beckmann rearrangement to satisfy the requirement of each reaction. Preferably, a single solvent is used to satisfy the requirement of both reactions in order to reduce the use and recycling of solvent. More preferably, the selected solvent is not water-soluble so that it can be easily separated after the oximation reaction and Beckmann rearrangement. The amount of solvent used in both reactions is not particularly limited as the solvent only functions to dissolve the reactants and products.

Solvents that show the required properties for both the oximation and Beckmann rearrangement belong to the classes of ester, aliphatics, aromatics, and ethers. Preferable solvents are butyl acetate, ethyl acetate, benzene, toluene, xylene, cumene, anisole, diethyl ether, diisopropyl ether, dibutyl ether, methyl tert-butyl ether, ethyl tert-butyl ether, methyl tetrahydrofuran, dimethyl carbonate, diethyl carbonate, petroleum ether, cyclohexane, dichloroethane, methylene chloride, chloroform, carbon tetrachloride, and trifluoromethylbenzene.

A single solvent or a mixture of two or more solvents can be used.

The oximation reaction is carried out at a temperature from 0° C. to 100° C., but can also be carried out at higher temperature under pressure. This reaction is preferably carried out at a temperature from 0° C. to 100° C. under atmospheric pressure. If the temperature is low, the reaction rate is slow, and reaction time is unnecessarily prolonged. Preferably, the reaction temperature is selected to be 60° C. to 80° C.

The oximation reaction is carried out in the air, but can also be carried out under the protection of an inert atmosphere, i.e., nitrogen, argon, or helium.

Time for the completion of oximation is related to the reaction temperature, usually in about 0.5 to 24 hours. Preferably, the reaction time is maintained for 1 to 6 hours, and the reaction temperature is controlled at 0° C. to 100° C. If the reaction time is too short, the residual content of keto amide (IIa) is too high, the yield will be reduced. Although the residual keto acid derivative can be recovered in the post treatment, additional equipment for recovery will be needed. Prolonged reaction can reduce the residual amount of keto acid derivative, but the volume of reactors becomes unnecessarily large.

Reactor for the oximation can be any reactor conventionally used in the chemical processing, for example, batch stirred reactor, semi-continuous reactor, tubular reactor, or flow reactor. Preferable reactor is continuous stirred tank reactor (CSTR). If CSTR is adopted, aqueous hydroxylamine solution and keto amide (IIa) in an organic solvent are simultaneously added in one reactor and then the reaction is completed in a cascade of reactors.

In the oximation reaction, if an aqueous solution of hydroxylamine salt is used, such as sulfate or hydrochloride, an alkaline agent, preferably ammonia, is needed to adjust the pH of the reaction solution to a range of 3 to 7 so that the reaction can proceed to completion. After the reaction and separation, the aqueous phase is concentrated to recover ammonium salt, i.e., ammonium sulfate. The oximation reaction can also be carried out by using ammoximation of ketoamide (IIa), according to prior art, i.e., hydrogen peroxide and ammonia in the presence of catalyst.

The molar ratio of ketoamide (IIa) and hydroxylamine can be from 0.1 to 10.0, preferably 1.0 to 2.0, most preferably 1.05 to 1.1 to ensure that ketoamide (IIa) is completely converted to oximeamide (IIIc).

After completion of the oximation reaction, oximeamide (IIIc) remains dissolved in organic phase, and aqueous phase is separated. Although the solubility of water in organic phase is small, but the remaining trace amount of water will destroy the catalytic activity of Beckmann catalyst and must be removed. In order to remove trace amount of water from organic phase, drying agent may be used. Preferably, the remaining water is removed by distilling part of the solvent. The distilled solvent can be used directly in the step of oximation without being dried. After distillation, the residual anhydrous solution of oxime derivative can be directly used for Beckmann rearrangement.

After thorough drying, the oximeamide (IIIc) is subjected to Beckmann rearrangement to mixed diamides (IVe and IVf) by heating in the presence of one or more catalysts. Suitable catalysts are sulfuric acid or activated halogen compounds or a mixture of activated halogen compounds and Lewis acids. Activated halogen compounds can be used for Beckmann rearrangement, but can be used in combination with Lewis acids to achieve better result. Preferably, activated halogen compounds are activated chlorine compounds.

Suitable activated chlorine compounds are thionyl chloride, sulfuryl chloride, chlorosulfonic acid, various sulfonyl chlorides: i.e., methanesulfonyl chloride, toluenesulfonyl chloride, various carbonyl chlorides: i.e., formyl chloride, acetyl chloride, benzoyl chloride, oxalyl chloride, phosgene, diphosgene, triphosgene, boron trichloride, chlorine-containing phosphorus compounds, i.e., phosphorus trichloride, phosphorus pentachloride, oxyphosphoryl chloride, and chlorine-containing heterocycles: i.e., cyanuric chloride, phosphorazine. One or a combination of two or more compounds can be used as catalyst.

Suitable Lewis acids are metal halides, i.e., zinc chloride, ferric chloride, cobalt chloride, stannous chloride, aluminum chloride, titanium chloride, boron trichloride. One or a combination of two or more in any molar ratio can be used.

In the Beckmann rearrangement as described above, activated chlorine-containing compound is used in catalytic amount, i.e., less than 10% of the molar amount of the oxime derivative, preferably in an amount of 0.1 to 5%. As with activated chlorine-containing compound, Lewis acid is also used in catalytic amount, i.e., less than 10% of the molar amount of the oxime derivative, preferably in an amount of 0.1 to 5%.

When sulfuric acid is used in the Beckmann rearrangement, the amount can be determined according to methods known in prior art for Beckmann rearrangement.

The molar ratio of Lewis acid and activated chlorine-containing compound is 1:0.01 to 1:100, preferably between 1:0.3 to 1:1.5.

The amount of catalyst, reaction temperature, reaction pressure, and reaction time are related. Under certain temperature, reaction time can be shortened by increasing the amount of catalyst.

The temperature for the Beckmann rearrangement of oxime derivative is not strictly limited, from room temperature to refluxing temperature. The reaction can also be performed at higher temperature under increased pressure. But if the temperature is too high, the color of rearranged products will darken, rendering post-treatment difficult.

The Beckmann rearrangement can be carried out in atmosphere, but also under inert gases, i.e., nitrogen, argon, or helium as protective atmosphere. This reaction is preferably carried out in dried air. The pressure for carrying out the rearrangement reaction is not limited, from standard normal pressure, to reduced or increased pressure.

The reactor for the Beckmann reaction is not limited. Reactors commonly used in chemical industry, and tubular reactors are suitable. The reaction can be carried out in batch, semi-continuously, or continuously.

After the Beckmann rearrangement, active catalyst may be quenched, but can also be reused after separating off the rearranged products. The active catalyst can be quenched by adding a small amount of water. The added water may also contain small amount of acid, or base, or some inorganic salts.

After the Beckmann rearrangement, the product diamide derivative is a mixture of two amides of the structure IVe and IVf, in an almost equal molar ratio. After recovery of solvent, this mixture can be purified to obtain pure amide derivative before proceeding to a hydrolysis step. On the other hand, crude product of the rearrangement reaction can be directly subjected to hydrolysis, and the impurities can be removed after hydrolysis. In fact, if the purity of ketoamide (IIa) is good, the rearrangement product is nearly pure.

It is noted that both the oximation reaction and the Beckmann rearrangement may be carried out in the absence of a solvent, because the amide group in the ketoamide, oximeamide, or mixed diamides acts as an excellent internal solvent. When no additional solvent is used, both the oximation reaction and Beckmann rearrangement are preferably carried out above the melting point of the reactant and product, in the range of 65° C. to 95° C.

Alternatively, the mixed diamides (IVe and IVf) may be used as a solvent for both the oximation reaction and Beckmann rearrangement. After Beckmann rearrangement, only part of the product solution is removed and the rest is continuously reused as a solvent.

After Beckmann rearrangement, the mixed diamides (IVe and IVf) may be used directly in the hydrolysis step to yield 11-aminoundecanoic acid (VIa) and dodecanedioic acid (Va). On the other hand, the mixed diamides (IVe and IVf) are preferably purified to remove colored impurities so that extensive purification of the hydrolysis products is not needed.

To remove colored impurities, the mixed diamides may be recrystallized from a solvent or from a melt. Suitable solvent may be selected from a group of lower alcohols, carboxylic acid, esters, ethers, aromatics, and amides. Preferably, the mixed amides (IVe and IVf) are recrystallized from its melt by a process technology known as melt crystallization, wherein no solvent is needed. When melt crystallization is carried out on the mixed diamides, colored material remains in the liquid. Most preferably, the mixed amides (IVe and IVf) are subjected to a distillation under high vacuum to yield a colorless product. Molecular distillation or short path distillation is well suited for this purpose.

When purified, colorless mixed diamides (IVe and IVf) are used in the hydrolysis reaction, the products of 11-aminoundecanoic acid (VIa) and dodecanedioic acid (Va) are nearly colorless and do not require further treatment for decolorization and show excellent property for polymerization.

Hydrolysis of the mixed diamides (IVe and IVf) and separation of the products may be carried out according to processes disclosed in U.S. Pat. Nos. 9,969,676; 9,969,678; 10,053,416; and 10,065,921, all of which are incorporated herein by reference.

Figure 4:
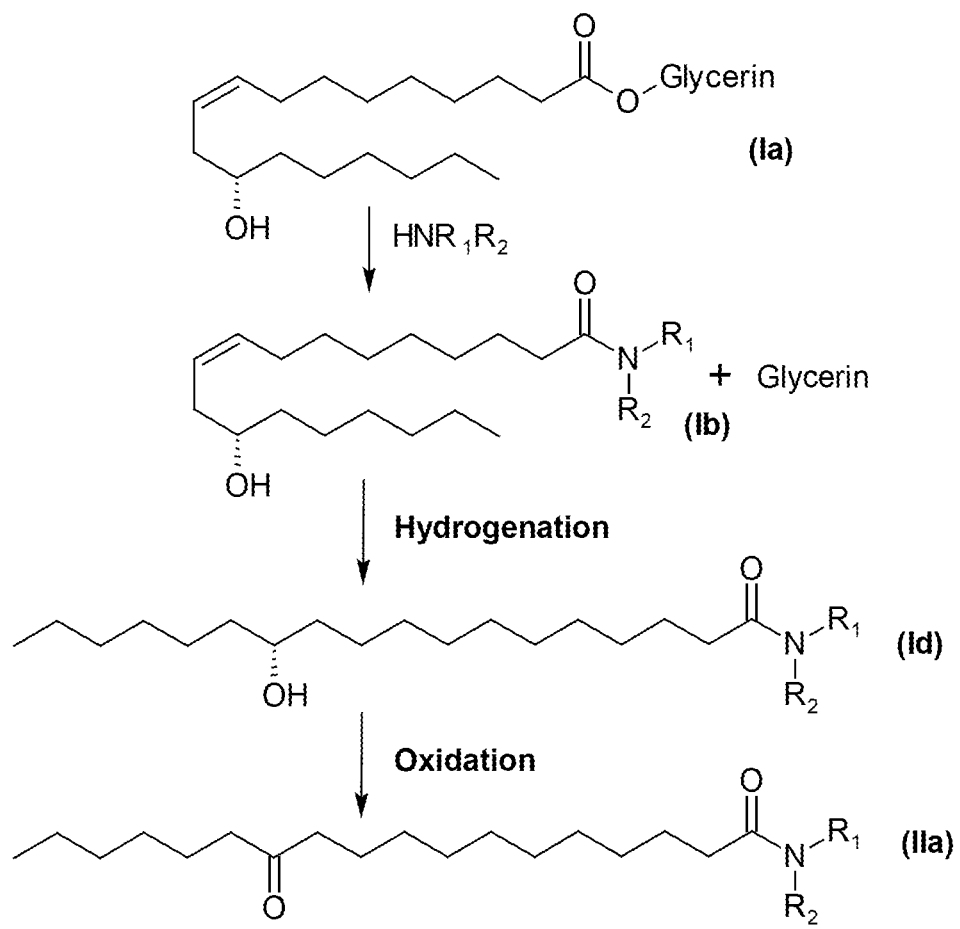
FIG. 4. illustrates one embodiment of reaction scheme for preparing keto-amide intermediate from castor oil.

FIG. 4 illustrates the second embodiment of a reaction scheme for producing the key intermediate of ketoamide (IIa) from castor oil. The three step process starts with the reaction of castor oil (Ia) with a primary or secondary amine $HNR_1R_2$ to form an intermediate (Ib), which has already been described in detail as a step in the process illustrated in FIG. 3. The intermediate (Ib) is first hydrogenated to the hydroxyamide (Id) in the presence of a hydrogenation catalyst, and then oxidized to the important ketoamide (IIa). The ketoamide (IIa) is then transformed to 11-aminoundecanoic acid and dodecanedioic acid according to the process described in FIG. 3.

The hydrogenation of (Ib) can be carried out neat or in the presence of at least one solvent in the presence of a hydrogenation catalyst. Suitable catalysts are selected from Raney Ni and Pd/C.

The oxidation of the hydroxyamide (Id) to the ketoamide (IIa) can be carried out according to methods described by G. Toto and M. Fernadez in *Oxidations of Alcohols to Aldehydes and Ketones*. The obtained (IIa) can be used as a crude product. Or the crude product can be readily purified by a recrystallization from at one solvent. Suitable solvents are found among the lower alcohols and aromatics. Particularly suitable solvents are methanol or toluene.

The ketoamide (IIa) is used to produce dodecanedioic acid and 11-aminoundecanoic acid according to process described in FIG. 3.

Figure 5:
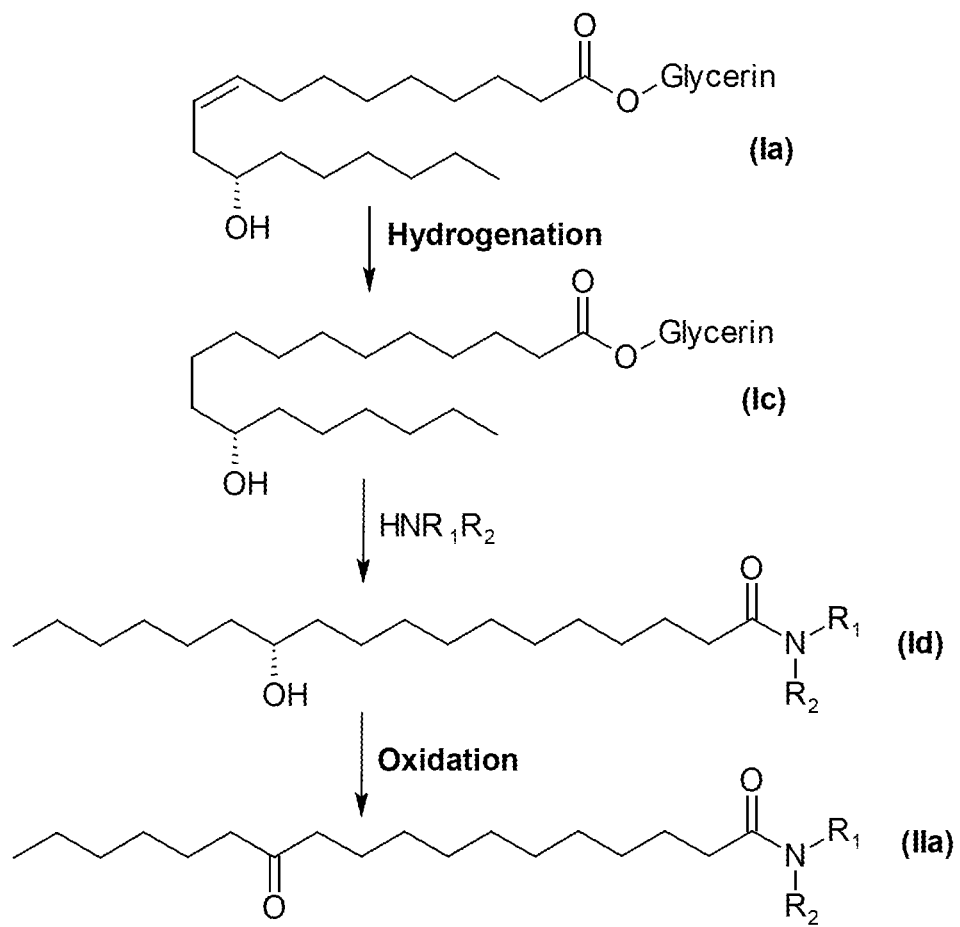
FIG. 5. illustrates one embodiment of reaction scheme for preparing keto-amide intermediate from hydrogenated castor oil.

FIG. 5 illustrates the third embodiment of a reaction scheme for producing the key intermediate of ketoamide (IIa) from castor oil. The three step process starts with the hydrogenation of castor oil (Ia) to hydrogenated castor oil (Ic), followed by the reaction with a primary or secondary amine $HNR_1R_2$ to form the hydroxyamide (Id), which is then oxidized to the ketoamide (IIa).

The hydrogenation of castor oil to hydrogenated castor oil (Ic) is a well known industrial process. It is usually carried out in the presence of Raney Nickel in neat castor oil, but can be performed in the presence of a solvent. It is found that the amide of ricinoleic acid (Ib) may be hydrogenated to the hydroxyamide (Id) under similar conditions.

The amidation reaction of hydrogenated castor oil (Ic) with a primary or secondary amine $HNR_1R_2$ may be carried out under the same reaction conditions as with castor oil to form the hydroxyamide (Id). Care should be excised so that the amine will not react with the hydroxyl group. To avoid the formation of byproduct from this reaction, the amidation reaction is preferably performed at a temperature below 200° C.

The hydroxyamide (Id) is then subjected to an oxidation reaction to the ketoamide (IIa), which is used to produce dodecanedioic acid and 11-aminoundecanoic acid according to process described and detailed in FIG. 3.

The present invention has three distinct advantages. First, the starting material of castor oil is widely and economically available, more than 1 million tons are produced from castor bean yearly. Secondly, there is no need to introduce additional alcohol group to protect the carboxylic acid. The most preferable primary amine, hexylamine, is an inherently produced product of the process, thus greatly simplifying the separation. Thirdly, the hexyl amide group is much more stable than an ester group under process conditions, thus rendering the process a much more robust.

It is particularly important to point out that dodecanedioic acid and 11-aminoundecanoic acid produced according to the present invention is of particularly high purity, containing no other long chain dibasic acid, nor long chain iminodibasic acid.

EXAMPLES

The following examples illustrate the practice of this invention but are not intended to limit its scope.

Example 1

This example relates to the production of 11-aminoundecanoic acid and dodecanedioic acid.

90 g of 12-ketostearic acid was mixed with 200 mL of water, followed by an aqueous solution of hydroxylamine sulfate (about 8%) containing 14.5 g of hydroxylamine. The mixture was vigorously stirred at 70-85° C., while the pH of the solution was adjusted to 4.5 to 5.0 with aqueous ammonia. After reacting for 2 hours, the starting material was completely transformed to 12-oxime stearic acid as indicated by HPLC analysis.

After the oximation reaction was complete, the mixture was settled to separate off aqueous phase and the upper oil phase was dried under vacuum. The product was dissolved in 500 mL of 98% methanesulfonic acid and heated to 140° C. for 4 hours to complete the Beckmann rearrangement. The reaction was terminated by adding 500 mL of water. The product of mixed amide fatty acids of reddish color was obtained after filtration and washing with deionized water.

The mixed amide fatty acids were dissolved in 500 mL of 10% sodium hydroxide, placed in an autoclave, and stirred at 150° C. for 4 hours under autogenous pressure. HPLC analysis indicated that the hydrolysis proceeded to completion.

The hydrolysis solution was distilled azeotropically to recover 12.8 g of hexylamine until no hexylamine came out the distillation head as indicated by a neutral pH at the head.

To the reaction solution were added 500 mL of water, 2 g of activated carbon to decolorize at 90° C. for 30 minutes. After filtration to remove activated carbon, sulfuric acid was added to the filtrate to adjust the pH to 7.5 to precipitate 11-aminoundecanoic acid. After cooling to room temperature, the precipitate was filtered, washed extensively with deionized water, and dried to yield 25.8 g of 11-aminoundecanoic acid.

The mother liquor after separating 11-aminoundecanoic acid was heated to 85° C., acidified with sulfuric acid to a pH of 4.5, a large amount of solid precipitated. After cooling to room temperature, the solid was separated by filtration, washed with distilled water three times, methanol once. After drying, 29.4 g of dodecanedioic acid was obtained.

The mother liquor after separating dodecanedioic acid was concentrated to 200 mL and the precipitated sodium sulfate was removed by filtration. To the mother liquor was added sulfuric acid to a pH of 1.0, an oil phase was formed and separated to give 16.9 g of heptanoic acid.

Example 2

This example relates to the production of 9-aminononanoic acid and sebacic acid.

90 g of 10-ketostearic acid was mixed with 200 mL of water, followed by an aqueous solution of hydroxylamine sulfate (about 8%) containing 12.5 g of hydroxylamine. The mixture was vigorously stirred for 2 hours at 70-80° C., while the pH of the solution was adjusted to 4.5 to 5.0 with aqueous ammonia. HPLC analysis indicated that the starting material was completely transformed to 10-oxime stearic acid.

After aqueous phase was separated off, the oil phase was dried under vacuum and dissolved in a mixture of 100 g of trifluoroacetic acid and 100 g of acetonitrile. The solution was refluxed for 8 hours to complete the Beckmann rearrangement. After distilling off solvent, 300 mL of water was added to precipitate the product of the mixed amide fatty acids of an off-white color.

The solid material of mixed amide fatty acids was dissolved in 200 mL of acetic acid, followed by 200 mL of 30% hydrochloric acid. The solution was refluxed for 48 hours to complete the hydrolysis. To the hot solution was added 500 mL of water. After cooling to room temperature, crystalline material was obtained by filtration and washing with deionized water. After drying, 34.6 g of sebacic acid was obtained.

The mother liquor was distilled under vacuum to a residual oil, which was partitioned with water to give 21.8 g of pelargonic acid.

The mother liquor after the separation of pelargonic acid was diluted to 800 mL with water, and heated to 80° C., slowly added a solution of sodium hydroxide to a pH of 6.5-7.0. After cooling, the precipitated solid was separated by filtration, washed with deionized water, and dried to yield 25.6 g of 9-aminononanoic acid.

The mother liquor after the separation of 9-aminononanoic acid was concentrated to 200 mL and the solid sodium chloride was removed by filtration. To the filtration mother liquor was added 20 mL of 50% sodium hydroxide, an oil layer was formed immediately. The oil layer was distilled to yield 14.6 g of octylamine.

Example 3

This example relates to the production of 13-aminotridecanoic acid and brassylic acid.

100 g of 14-ketoarachidic acid was mixed with 200 mL of water, followed by an aqueous solution of hydroxylamine sulfate (about 8%) containing 16.5 g of hydroxylamine. The mixture was vigorously stirred for 2 hours at 75-85° C., while the pH of the solution is adjusted to 4.5 to 5.0 with aqueous ammonia. HPLC analysis indicated that the starting material was completely transformed to 14-oxime arachidic acid.

After aqueous phase was separated off, the oil phase was dried in vacuum. The residual waxy solid was slowly added to 300 mL of 98% sulfuric acid at 100° C. The solution was stirred at the same temperature for 2 hours to complete the Beckmann rearrangement, which was terminated by adding 800 g of ice. The product of the mixed amide fatty acids of dark color was obtained by filtration and washing with water.

The solid material was dissolved in 700 mL of 8% sodium hydroxide, placed into an autoclave and heated to 150° C. for 5 hours to complete the hydrolysis reaction. HPLC showed complete disappearance of the starting material.

The hydrolysis solution was distilled azeotropically to recover 13.4 g of hexylamine until no hexylamine came out the distillation head as indicated by a neutral pH at the head.

To the reaction solution were added 500 mL of water, 2 g of activated carbon to decolorize at 90° C. for 30 minutes. After filtration to remove activated carbon, sulfuric acid was added to the filtrate to adjust pH to 7.5. After cooling to room temperature, 13-aminotridecanoic acid crystallized. The solid was filtered, washed extensively with deionized water, and dried to yield 32.7 g of 13-aminotridecanoic acid.

The mother liquor after separating 13-aminotridecanoic acid was heated to 85° C., acidified with sulfuric acid to a pH of 4.5, a large amount of solid precipitated. After cooling to room temperature, the solid was separated by filtration, washed with distilled water three times, methanol once. After drying, 40.6 g of brassylic acid was obtained.

The mother liquor after separating brassylic acid was concentrated to 200 mL and the precipitated sodium sulfate was removed by filtration. To the mother liquor is added sulfuric acid to a pH of 1.0, an oily phase was formed and separated to give 16.2 g of heptanoic acid.

Example 4

This example relates to the ammoximation of 12-ketostearic acid 90 g of 12-ketostearic was dissolved in 500 mL of toluene, followed by 20 g of TS-1 catalyst. The mixture was vigorously stirred at 70° C., while 50 mL of 27.5% hydrogen peroxide and 70 mL of 25% ammonia were added slowly at the same time. The stirring was continued for an additional 60 minutes at 75° C. after the addition of hydrogen peroxide and ammonia. HPLC analysis showed a complete conversion of starting material to 12-oxime stearic acid. Following the procedure in Example 1, 28.2 g of 11-aminoundecanoic acid and 31.9 g of dodecanedioic acid were obtained.

Example 5

This example relates to the Beckmann rearrangement of 12-oxime stearic acid catalyzed by thionyl chloride-zinc chloride catalyst.

30 g of 12-oxime stearic acid was placed in 400 mL of acetonitrile, to which was added 0.4 g of zinc chloride and 1.2 g of thionyl chloride. The mixture was refluxed for 2 hours. HPLC analysis indicated complete conversion of the oxime stearic acid into the mixed amide fatty acid.

Acetonitrile was distilled and to the residual was added 200 mL of water. After being stirred for 30 minutes at room temperature, the mixed amide acid was recovered by filtration.

Example 6

This example is related to the preparation of keto fatty acid by oxidizing hydroxy fatty acid in acetic acid.

30 g of 12-hydroxystearic acid was dissolved in 600 mL of 95% aqueous acetic acid and cooled on ice. To the stirred solution was added slowly 100 mL of 8.0% sodium hypochlorite, while the temperature was maintained at 5-10° C. After the addition was completed, stirring was continued for 60 minutes. Acetic acid was recovered by distillation and 300 mL of water was added to the distillation residual. After filtration, 29.5 g of 12-ketostearic acid was obtained.

Example 7

This example relates to the production of 11-aminoundecanoic acid and dodecanedioic acid.

90 g of 12-ketostearic acid was mixed with 200 mL of water, followed by an aqueous solution of hydroxylamine sulfate (about 8%) containing 14.5 g of hydroxylamine. The mixture was vigorously stirred at 80-85° C., while the pH of the solution was adjusted to 4.5 to 5.0 with aqueous ammonia. After reacting for 2 hours, the starting material was completely transformed to 12-oxime stearic acid as indicated by HPLC analysis.

After the oximation reaction was complete, the mixture was settled to separate off aqueous phase and the upper oil phase was dried under vacuum. The product was dissolved in 500 mL of methanol and a few drops of sulfuric acid. The solution was refluxed for 2 hrs to complete the formation of methyl ester. A few drops of triethylamine were added to a neutral pH. Methanol was removed and the residual was dissolved in 500 mL toluene and the solution was washed with deionized water three times and dried azeotropically.

To the toluene solution was added 1 g of anhydrous zinc chloride and 2 g of triphosgene to affect the Beckmann rearrangement. After the solution was stirred at 80-90° C. for 3 hrs, no starting material was detected. To the solution was added 100 mL of water to quench the reaction. Toluene was removed by distillation to obtain the mixed amide methyl ester.

The mixed amide fatty acid methyl ester were dissolved in 500 mL of 10% sodium hydroxide, placed in an autoclave, and stirred at 150° C. for 4 hours under autogenous pressure. HPLC analysis indicated that the hydrolysis proceeded to completion.

The hydrolysis solution was distilled azeotropically to recover 12.8 g of hexylamine until no hexylamine came out the distillation head as indicated by a neutral pH at the head.

To the reaction solution were added 500 mL of water, 2 g of activated carbon to decolorize at 90° C. for 30 minutes. After filtration to remove activated carbon, sulfuric acid was added to the filtrate to adjust the pH to 7.5 to precipitate 11-aminoundecanoic acid. After cooling to room temperature, the precipitate was filtered, washed extensively with deionized water, and dried to yield 25.5 g of 11-aminoundecanoic acid.

The mother liquor after separating 11-aminoundecanoic acid was heated to 85° C., acidified with sulfuric acid to a pH of 4.5, a large amount of solid precipitated. After cooling to room temperature, the solid was separated by filtration, washed with distilled water three times, methanol once. After drying, 28.4 g of dodecanedioic acid was obtained.

The mother liquor after separating dodecanedioic acid was concentrated to 200 mL and the precipitated sodium sulfate was removed by filtration. To the mother liquor was added sulfuric acid to a pH of 1.0, an oil phase was formed and separated to give 15.6 g of heptanoic acid.

Example 8

This example relates to the production of dodecanedioic acid and 11-aminoundecanoic acid from castor oil.

Into a three-neck 1 L flask were added 350 g of castor oil and 120 mL of hexylamine. The solution was gradually heated to 160° C. and maintained at the same temperature for 2 hrs. After the solution was cooled to 90° C., 500 mL of warm water was added and the mixture was stirred at 80-90° C. for 1 hr before the aqueous phase was separated off. The oil phase was washed with dilute sulfuric acid to remove excess hexylamine and dried under vacuum. The oil solidified after cooled to room temperature.

200 g of the waxy solid was placed in a 1 L flask and heat to 100° C. to form a clear liquid. The flask was then purged with nitrogen. To the solution was then added 5 g of pentacarbonyl iron and the solution was heated to 190° C. to 200° C. for 3 hrs under stirring. After the solution was cooled to room temperature, 500 mL of methanol was added to the flask and the suspension was heated to refluxing to form a clear solution, which was cooled to form a crystalline suspension. Filtration and washing with methanol yielded 125 g of the ketoamide (IIa).

The ketoamide (IIa) was dissolved in 500 mL of toluene in a 1 L flask, to which was added 500 mL solution of hydroxylamine. The two phase mixture was vigorously stirred at 90° C. for 4 hrs to complete the oximation reaction to form oximeamide (IIIc). The aqueous phase was separated and the toluene phase was washed with water. The toluene phase was dried by distilling off 50 mL of toluene.

To the toluene solution were then added 2 g of cyanuric chloride and 1.5 g of zinc chloride to start Beckmann rearrangement at 90° C. for 2 hrs. The reaction was quenched by adding 50 mL of water. After separating the aqueous phase and recovering toluene, a mixture of diamides (IVe and IVf) was obtained as a solid of straw-color, which was used directly in the hydrolysis.

The mixed diamides were hydrolyzed to form dodecanedioic acid and 11-aminoundecanoic acid following the procedure described in Example 1.

Example 9

This example relates to the production of ketoamide from castor oil.

50 g of the waxy product obtained from the reaction of castor oil and hexylamine in Example 8 was dissolved in 500 mL of methanol and hydrogenated at 60 psi in the presence of 4 mL of Raney Ni. After filtration to remove Raney Ni, methanol was removed to yield the hydroxyamide (Id).

The hydroxyamide (Id) was added to 750 mL of acetic acid and the suspension was cooled under vigorous stirring to below 10° C. on an ice bath. To the suspension was added 150 mL of 6% sodium hypochlorite solution. The mixture was stirred for 2 hrs at 5° C., 1 hr at room temperature to yield the ketoamide (IIa). The product was isolated by removing acetic acid and washed with water.

Example 10

This example relates to the production of ketoamide from hydrogenated castor oil.

150 g of hydrogenated castor oil and 100 mL of hexylamine were mixed in a 500 mL flask and gradually heated to 160° C. and maintained at the same temperature for 2 hrs. After the solution was cooled to 90° C., 200 mL of warm water was added and the mixture was stirred at 80-90° C. for 1 hr before the aqueous phase was separated off. The oil phase was washed with dilute sulfuric acid to remove excess hexylamine. Then 250 mL of water was added and the mixture was cooled to room temperature under stirring to solidify the oil phase. Filtration and washing with water yielded the hydroxyamide (Id).

50 g of the hydroxyamide (Id) was added to 750 mL of acetic acid and the suspension was cooled under vigorous stirring to below 10° C. on an ice bath. To the suspension was added 150 mL of 6% sodium hypochlorite solution. The mixture was stirred for 2 hrs at 5° C., and 1 hr at room temperature to yield the ketoamide (IIa). The product was isolated by removing acetic acid and washed with water.

It will be understood that the foregoing examples, explanation, and drawing are for illustrative purpose only and that in view of the instant disclosure various modifications of the present invention will be self-evident to those skilled in the art and are to be included within the spirit and purview of this application and the scope of the appended claims.

What is claimed is:

1. A process for producing dodecanedioic acid and 11-aminoundecanoic acid, comprising:

(a) reacting castor oil with a primary or secondary amine HNR$_1$R$_2$ to form an amide of formula (Ib):

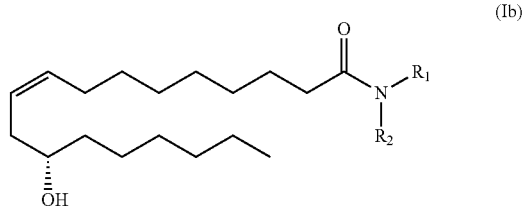

in the absence or in the presence of at least one solvent, wherein R$_1$ and R$_2$ are each independently hydrogen, or C$_1$ to C$_{12}$ aliphatic or aromatic groups;

(b) isomerizing the amide of formula (Ib) in the presence of at least one catalyst to form a ketoamide of formula (IIa):

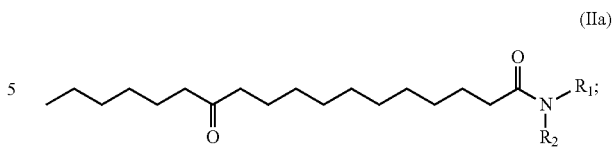

(c) subjecting the ketoamide of formula (IIa) to an oximation reaction with hydroxylamine or an ammoximation reaction with ammonia and hydrogen peroxide in the presence of an ammoximation catalyst to form an oximeamide of formula (IIIc):

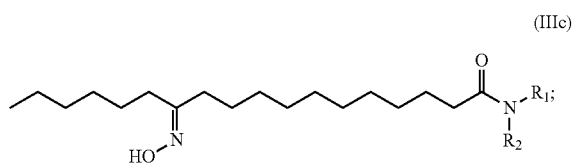

(d) subjecting the oximeamide of formula (IIIc) to Beckmann rearrangement to yield a mixture of diamides of formulas (IVe) and (IVf):

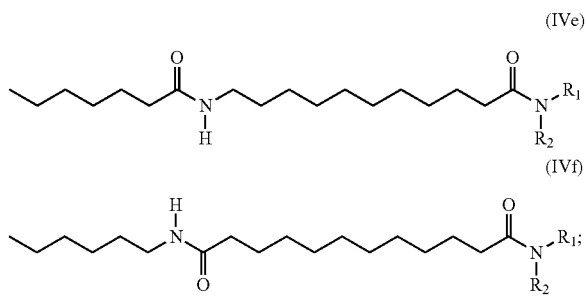

(e) hydrolyzing the mixed diamides of formulas (IVe) and (IVf) with an acid or a base to dodecanedioic acid (Va), 11-aminoundecanoic acid (VIa), hexylamine (VIIa), and heptanoic acid (VIIIa) of the structures:

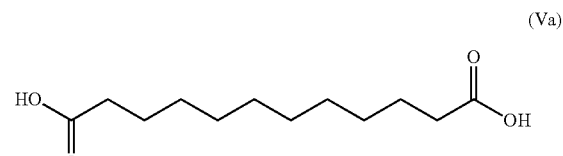

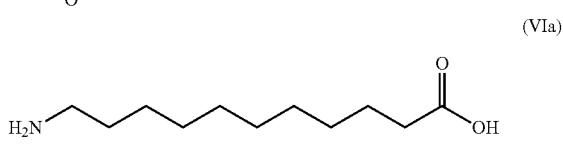

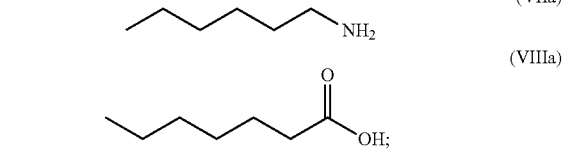

and (f) separating the dodecanedioic acid (Va), 11-aminoundecanoic acid (VIa), hexylamine (VIIa), and heptanoic acid (VIIIa).

2. A process for producing dodecanedioic acid and 11-aminoundecanoic acid, comprising:

(a) reacting castor oil with a primary or secondary amine HNR₁R₂ to form an amide of formula (Ib):

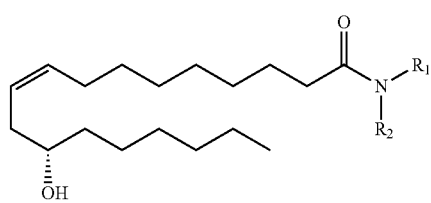
(Ib)

in the absence or in the presence of at least one solvent, wherein R₁ and R₂ are each independently hydrogen, or $C_1$ to $C_{12}$ aliphatic or aromatic groups;

(b) hydrogenating the amide formula (Ib) to form 12-hydroxystearic acid amide of the formula (Id):

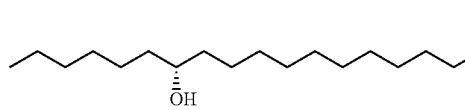
(Id)

(c) oxidizing the 12-hydroxystearic acid amide formula (Id) to form a ketoamide of formula (IIa):

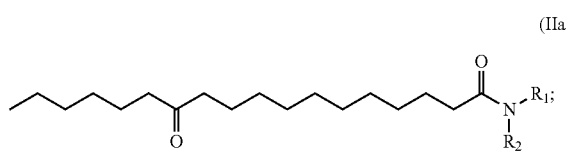
(IIa)

(d) subjecting the ketoamide of formula (IIa) to an oximation reaction with hydroxylamine or an ammoximation reaction with ammonia and hydrogen peroxide in the presence of an ammoximation catalyst to form an oximeamide of formula (IIIc):

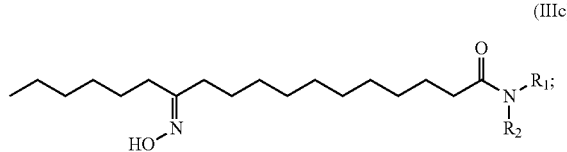
(IIIc)

(e) subjecting the oximeamide of formula (IIIc) to Beckmann rearrangement to yield a mixture of diamides of formulas (IVe) and (IVf):

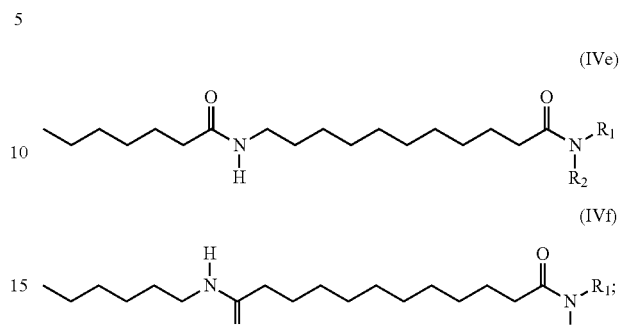
(IVe)
(IVf)

(f) hydrolyzing the mixed diamides of formulas (IVe) and (IVf) with an acid or a base to dodecanedioic acid (Va), 11-aminoundecanoic acid (VIa), hexylamine (VIIa), and heptanoic acid (VIIIa) of the structures:

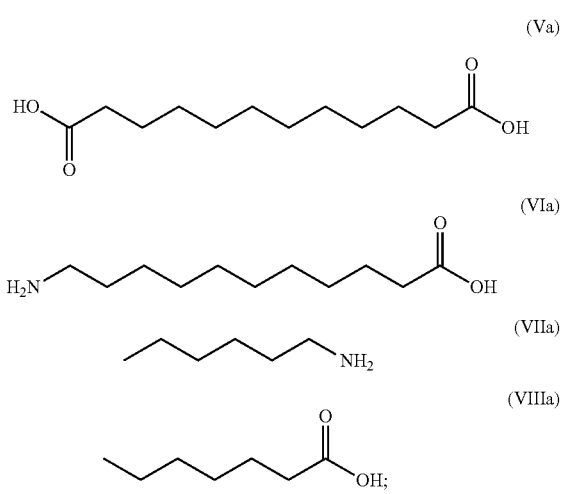
(Va)
(VIa)
(VIIa)
(VIIIa)

and (g) separating the dodecanedioic acid (Va), 11-aminoundecanoic acid (VIa), hexylamine (VIIa), and heptanoic acid (VIIIa).

3. A process for producing dodecanedioic acid and 11-aminoundecanoic acid, comprising:

(a) hydrogenating castor oil to form hydrogenated castor oil of formula (Ic):

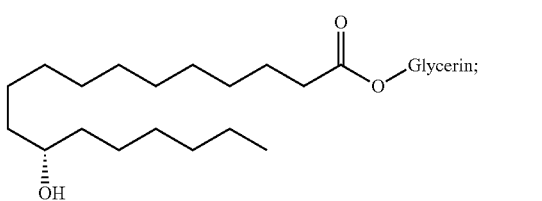
(Ic)

(b) reacting the hydrogenated castor oil of formula (Ic) with a primary or secondary amine $HNR_1R_2$ to form a hydroxyamide of formula (Id):

(Id)

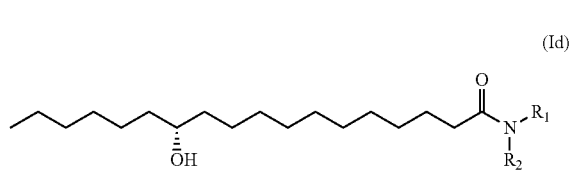

in the absence or in the presence of at least one solvent, wherein $R_1$ and $R_2$ are each independently hydrogen, or $C_1$ to $C_{12}$ aliphatic or aromatic groups;

(c) oxidizing the hydroxyamide of formula (Id) to form a ketoamide of formula (IIa):

(IIa)

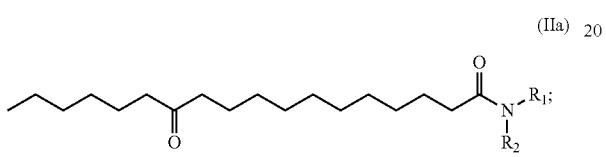

(d) subjecting the ketoamide of formula (IIa) to an oximation reaction with hydroxylamine or an ammoximation reaction with ammonia and hydrogen peroxide in the presence of an ammoximation catalyst to form an oximeamide of formula (IIIc):

(IIIc)

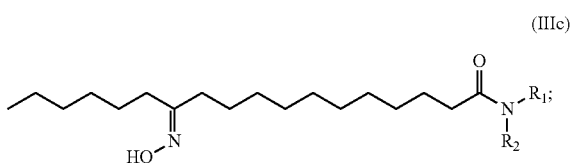

(e) subjecting the oximeamide of formula (IIIc) to Beckmann rearrangement to yield a mixture of diamides of the formulas (IVe) and (IVf):

(IVe)

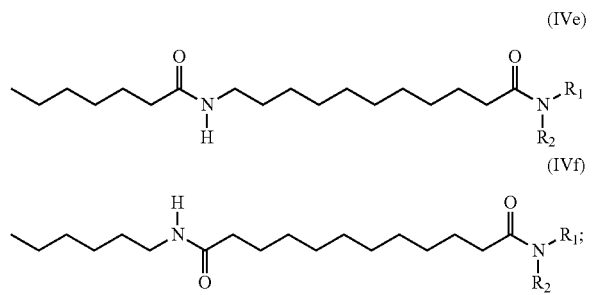

(IVf)

(f) hydrolyzing the mixed diamides of formulas (IVe) and (IVf) with an acid or a base to dodecanedioic acid (Va), 11-aminoundecanoic acid (VIa), hexylamine (VIIa), and heptanoic acid (VIIIa) of the structures:

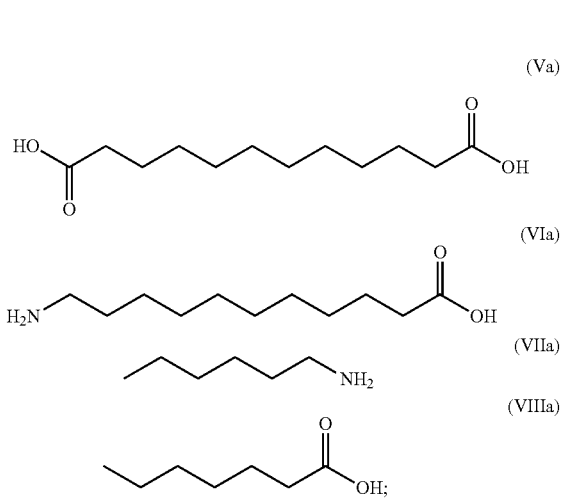

and (g) separating the dodecanedioic acid (Va), 11-aminoundecanoic acid (VIa), hexylamine (VIIa), and heptanoic acid (VIIIa).

4. The process according to claim 1, wherein the reaction of the castor oil and the $HNR_1R_2$ is performed at a temperature from 80° C. to 180° C.

5. The process according to claim 1, wherein the $HNR_1R_2$ is hexylamine.

6. The process according to claim 1, wherein the isomerization catalyst is selected from the group of pentacarbonyl iron, Raney Ni, and Pd/C.

7. The process according to claim 1, wherein a catalyst for the Beckmann rearrangement of the oximeamide of formula (IIIc) is selected from the group consisting of sulfuric acid, alkylsulfonic acid, arylsulfonic acid, or perfluorocarboxylic acids, thionyl chloride, sulfuryl chloride, chlorosulfonic acid, methanesulfonyl chloride, toluenesulfonyl chloride, acetyl chloride, benzoyl chloride, oxalyl chloride, phosgene, diphosgene, triphosgene, boron trichloride, phosphorus trichloride, phosphorus pentachloride, oxyphosphoryl chloride, cyanuric chloride, phosphorazine, zinc chloride, ferric chloride, cobalt chloride, stannous chloride, aluminum chloride, titanium chloride, boron trichloride, and a mixture of two or more thereof.

8. The process according to claim 2, wherein the $HNR_1R_2$ is hexylamine.

9. The process according to claim 3, wherein the reaction of the hydrogenated castor oil and the $HNR_1R_2$ is performed at a temperature from 80° C. to 180° C.

10. The process according to claim 3, wherein the $HNR_1R_2$ is hexylamine.

* * * * *